United States Patent
Tybinkowski et al.

(10) Patent No.: US 7,062,011 B1
(45) Date of Patent: Jun. 13, 2006

(54) CARGO CONTAINER TOMOGRAPHY SCANNING SYSTEM

(75) Inventors: Andrew P. Tybinkowski, Boxford, MA (US); Ronald Swain, Reading, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/732,087

(22) Filed: Dec. 10, 2003

Related U.S. Application Data

(60) Provisional application No. 60/432,348, filed on Dec. 10, 2002.

(51) Int. Cl.
*G01N 23/083* (2006.01)
*G01N 23/10* (2006.01)

(52) U.S. Cl. .................................... 378/57
(58) Field of Classification Search .............. 378/4, 378/10, 17, 57
See application file for complete search history.

(56) References Cited

U.S. PATENT DOCUMENTS

| | | | |
|---|---|---|---|
| 3,810,534 A | | 5/1974 | Prete, Jr. |
| 3,986,460 A | | 10/1976 | Voigt et al. |
| 4,089,275 A | | 5/1978 | Pelletier |
| 4,349,302 A | | 9/1982 | Ferguson, Jr. |
| 4,472,822 A | * | 9/1984 | Swift .................... 378/10 |
| 4,989,225 A | * | 1/1991 | Gupta et al. .......... 378/10 |
| 5,056,124 A | * | 10/1991 | Kakimoto et al. ........ 378/57 |
| 5,124,554 A | * | 6/1992 | Fowler et al. ......... 250/358.1 |
| 5,182,764 A | | 1/1993 | Peschmann et al. |
| 5,367,552 A | | 11/1994 | Peschmann |
| 5,420,427 A | * | 5/1995 | Morgan et al. ........... 378/59 |
| 5,433,564 A | | 7/1995 | Sundseth |
| 5,642,393 A | | 6/1997 | Krug et al. |
| 5,661,774 A | | 8/1997 | Gordon |
| 5,796,802 A | | 8/1998 | Gordon |
| 6,185,272 B1 | * | 2/2001 | Hiraoglu et al. .......... 378/57 |
| 6,188,745 B1 | | 2/2001 | Gordon |
| 6,301,327 B1 | | 10/2001 | Martens et al. |
| 6,301,334 B1 | * | 10/2001 | Tybinkowski et al. ...... 378/147 |
| 6,327,329 B1 | * | 12/2001 | Bromberg et al. ......... 378/19 |
| 6,418,189 B1 | | 7/2002 | Schafer |
| 6,430,255 B1 | * | 8/2002 | Fenkart et al. ........... 378/57 |
| 6,459,764 B1 | | 10/2002 | Chalmers et al. |
| 6,711,235 B1 | * | 3/2004 | Galish et al. ............. 378/57 |
| 2003/0031293 A1 | * | 2/2003 | Aust et al. .............. 378/57 |
| 2004/0109532 A1 | * | 6/2004 | Ford et al. .............. 378/57 |

* cited by examiner

*Primary Examiner*—Edward J. Glick
*Assistant Examiner*—Chih-Cheng Glen Kao
(74) *Attorney, Agent, or Firm*—McDermott Will & Emery LLP

(57) ABSTRACT

An X-ray computed tomography scanning system adapted to scan air cargo containers or other larger containers for detection of explosives, drugs, and other contraband. The system includes a table that rotates about an axis of rotation for supporting a cargo container, an X-ray source movable parallel to the rotation axis of the table on one side of the table, and an X-ray detector movable parallel to the rotation axis of the table on another side of the table.

29 Claims, 2 Drawing Sheets

CARGO CONTAINER TOMOGRAPHY SCANNING SYSTEM

CROSS-REFERENCE TO RELATED APPLICATION

The present application claims priority from U.S. Provisional Patent Application Ser. No. 60/432,348 filed on Dec. 10, 2002, which is assigned to the assignee of the present application and incorporated herein by reference.

FIELD OF THE INVENTION

The present disclosure relates generally to X-ray scanning systems and, more particularly, to an X-ray baggage scanning system. Even more particularly, the present disclosure relates to an X-ray computed tomography scanning system adapted to scan air cargo containers or other larger containers for detection of explosives, drugs, and other contraband.

BACKGROUND OF THE DISCLOSURE

The U.S. Department of Homeland Security and the Transportation Security Administration and other similar agencies throughout the world have the daunting task of identifying dangerous devices and/or contraband within passenger baggage and within a time-frame that will not generally impede passenger travel time. Many X-ray baggage scanning systems in use today are of the "line scanner" type and include a stationary X-ray source, a stationary linear detector array, and a conveyor belt for transporting baggage between the source and detector array as the baggage passes through the scanner. The X-ray source generates a stationary X-ray beam that passes through and is partially attenuated by the baggage, as the baggage is moved into and positioned within the beam, before being received by the detector array. During each measuring interval, each detector of the detector array generates data representative of the integral of the density of the planar segment of the baggage through which the detected portion of the X-ray beam passes. The data acquired by the detector array during each measuring interval is used to form one or more raster lines of a two dimensional image. As the conveyor belt transports the baggage past the stationary source and detector array, the scanner generates a two dimensional image representative of the density of the baggage, as viewed by the stationary detector array. The density image is typically displayed for analysis by a human operator.

It has been suggested to use X-ray computed tomography (CT) as a part of a baggage scanner to identify objects within baggage positioned in the scanner. At least one of these designs, described in U.S. Pat. No. 5,182,764 (Peschmann et al.) and U.S. Pat. No. 5,367,552 (Peschmann et al.) (hereinafter the '764 and '552 patents), for example, has been commercially developed and are referred hereinafter as the "In Vision Machine". The In Vision Machine includes a CT scanner of the third generation type. Third generation type CT scanners are particularly useful in the medical arts and are often used for imaging sections of the human body. Third generation scanners typically include an X-ray source and an X-ray detector system secured respectively to diametrically opposite sides of an annular-shaped gantry platform or disk. The gantry disk is rotatably mounted within a gantry support so that in operation the disk continuously rotates about a rotation axis while X-rays pass from the source through an object positioned within the opening of the disk to the detector system. During a scanning procedure, baggage passes along the rotation axis through the rotating gantry disk.

The EXACT™ AN6000, which is available from International Security Systems Corporation, which is a subsidiary of the assignee of the present disclosure, Analogic Corporation, is an advanced CT system for the detection of explosives, drugs, and other contraband in carry-on baggage. The EXACT™ AN6000 generates 3-D image data of all objects in a bag, gathers all data in one pass, allows automatic analysis of entire contents of bag, and can handle up to 600 bags per hour. Analogic's EXACT™ AN6000 is a dual energy, helical-cone-beam, multi-slice CT system that provides a complete set of CT images of an entire three-dimensional object as it passes along the baggage conveyor. The system includes a high efficiency, wide dynamic range, solid-state X-ray detector array consisting of 6048 detectors. Rotating at 90 RPM, this system takes up to 720 sets of 6048 measurements per rotation every two-thirds of a second. The system presents both projection and axial images of this moving object for analysis by the operator. The EXACT™ AN6000 CT system is covered by at least the following U.S. patents which are owned by Analogic Corporation: U.S. Pat. Nos. 5,661,774; 5,796,802; 5,818,897; 6,185,272; 6,188,745; and 6,418,189.

The EXACT™ AN6000 is the heart of the eXaminer 3DX™ 6000 Explosive Detection System (EDS), the first single-unit, second-generation CT system certified by the U.S. Federal Aviation Administration and developed in cooperation with L-3 Communications. The EXACT™ AN6000 is also the system of choice for detection of drugs and other contraband. Equipped by ISS with our own workstation and custom drug algorithms, the EXACT™ AN6000 has been successfully demonstrated to the U.S. Customs Service, detecting small quantities of contraband. Sophisticated software automatically isolates bag contents unambiguously and analyzes them, evaluating them against the known characteristics of explosives or narcotics. If a match is found, the system alerts the operator, highlights the area of concern for further analysis, and provides a full rotating 3-D image of the potential threat.

What is still desired is a system for detecting explosives, drugs, and other contraband in objects larger than a typical piece of carry-on luggage, such as an air cargo container containing a plurality of pieces of luggage. Preferably, the system will be an X-ray computed tomography scanning system adapted to scan air cargo containers or other larger containers for detection of explosives, drugs, and other contraband.

SUMMARY OF THE DISCLOSURE

The present disclosure provides a new and improved X-ray computed tomography scanning system adapted to scan air cargo containers or other larger containers for detection of explosives, drugs, and other contraband. The system includes a table that rotates about an axis of rotation for supporting a cargo container, a first platform supporting an X-ray source thereon and movable parallel to the rotation axis of the table, and a second platform supporting an X-ray detector thereon and movable parallel to the rotation axis of the table.

During a scanning procedure, the table rotates the cargo container about the axis of rotation, while the first and the second platforms move parallel to the rotation axis of the table, and the X-ray source sends an X-ray beam through the cargo container to the X-ray detector. The container is completely scanned when the X-ray beam clears an end of the container, at which time the X-ray source shuts off. The scanned cargo container is then removed from the table, another cargo container is positioned on the table and the table is rotated. The first and the second platforms then move in an opposite direction parallel to the rotation axis of the table and the X-ray source and the X-ray detector are operated to scan the container.

Other features and advantages of the presently disclosed disclosure will become apparent by reference to the following description taken in connection with the accompanying drawings.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 1:
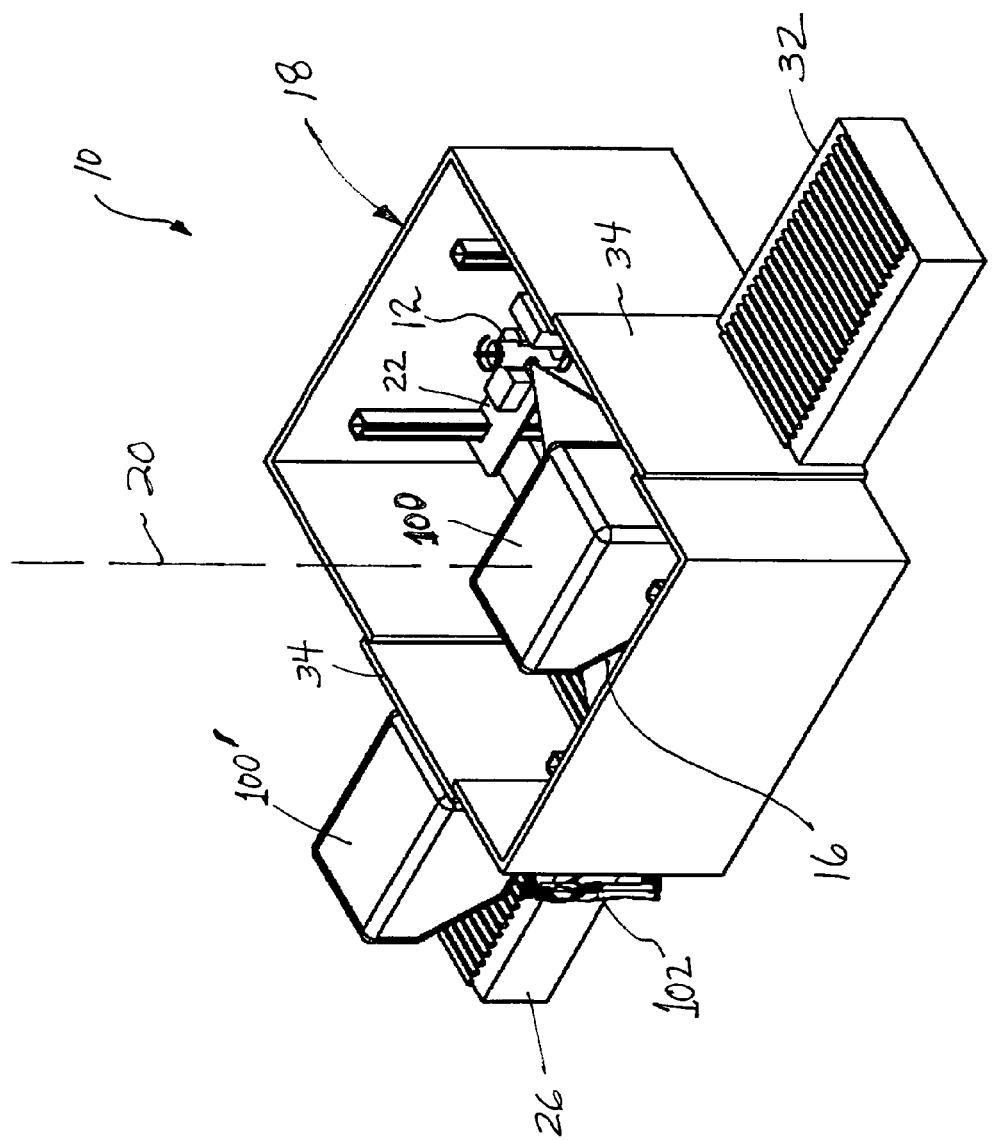
FIG. 1 is a perspective view of an exemplary embodiment of an X-ray computed tomography scanning system constructed in accordance with the present disclosure and adapted to scan air cargo containers or other large containers for detection of explosives, drugs, and other contraband, and wherein a first cargo container is shown being scanned, a second cargo container is shown prior to be scanned, and a person is shown standing next to the system to provide a size comparison.
Figure 2:
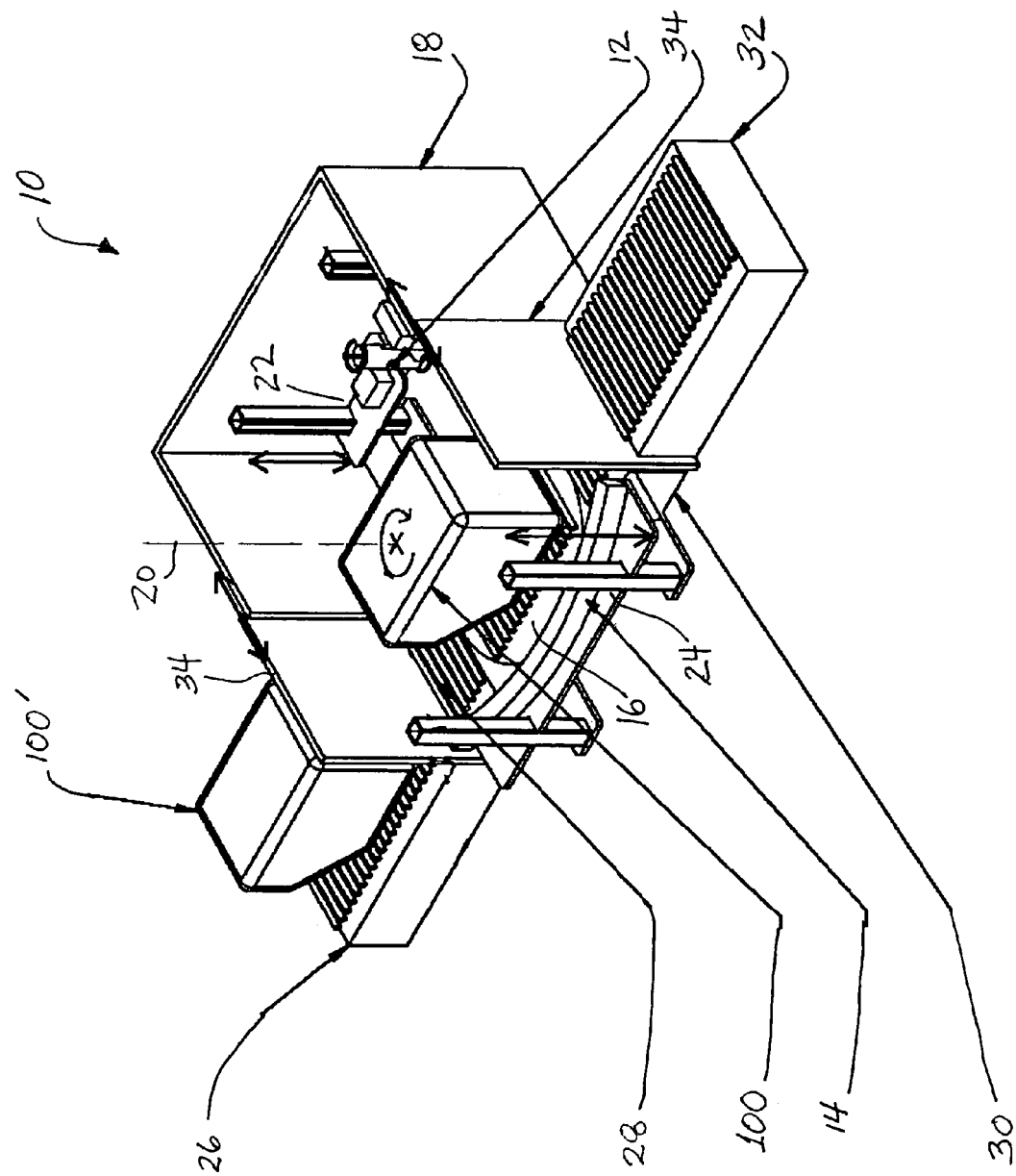
FIG. 2 is a perspective view of the X-ray computed tomography scanning system of FIG. 1 shown with a front containment wall removed.

FIGS. 1 and 2 are perspective views of an exemplary embodiment of an X-ray computed tomography (CT) scanning system 10 constructed in accordance with the present disclosure and adapted to scan air cargo containers 100 or other large containers for detection of explosives, drugs, and other contraband. In FIGS. 1 and 2 a first cargo container 100 is shown being scanned, a second cargo container 100' is shown prior to being scanned, and a person 102 is shown standing next to the system 10 to provide a size comparison. In addition, a top X-ray containment wall is shown removed. In FIG. 2, the scanning system 10 is shown with a front X-ray containment wall removed.

The system 10 of the present disclosure generally scans for the same items and provides the same results as the EXACT™ AN6000 CT system, which is available from International Security Systems Corporation, which is a subsidiary of the assignee of the present disclosure, Analogic Corporation. The system 10 of the present disclosure, however, is adapted to scan air cargo containers 100 or other large containers instead of just smaller carry-on baggage.

Like the EXACT™ AN6000, the system 10 of the present disclosure generates 3-D image data of all objects in a scanned container 100, gathers all data in one pass, and allows automatic analysis of entire contents of the container. The system 10 includes an X-ray source 12 and an X-ray detector 14. In one exemplary embodiment, the X-ray source 12 is a dual energy, helical-cone-beam, multi-slice CT system that provides a complete set of CT images of an entire three-dimensional object as it is scanned, and the X-ray detector 14 is a high efficiency, wide dynamic range, solid-state, two dimensional X-ray detector array.

The scanning system 10 also includes a rotating table 16 disposed within an X-ray containment enclosure 18. The table 16 is for supporting a cargo container 100 and rotates about a rotation axis 20. The table 16 is driven about the rotation axis 20 by a suitable drive assembly (not shown). A suitable drive assembly may comprise, for example, a pulley secured to the table 16, a drive belt connected to the pulley, and a motor for causing the drive belt to rotate the pulley and the table 16.

The X-ray source 12 and the detector array 14 are disposed on diametrically opposite sides of the table 16. A first platform 22 supports the X-ray source 12 and is movable parallel to the rotation axis 20 of the table 16. A second platform 24 supports the X-ray detector 14 and is also movable parallel to the rotation axis 20 of the table 16. In the exemplary embodiment shown, the rotation axis 20 of the table 16 extends in a vertical direction, and the first and the second platforms 22, 24 also move in vertical directions, i.e., up and down.

The first and the second platforms 22, 24 are controlled such that they move in a synchronized manner, with each other. Suitable drive mechanisms are used to raise and lower the first and the second platforms 22, 24. The drive mechanisms may, for example, comprise rotary motors driving vertically extending screws threaded through bearings secured to the platforms 22, 24, such that the motors turning the screws causes the platforms to be raise or lowered. In accordance with one exemplary embodiment, the first and the second platforms 22, 24 are controlled such that they move in a synchronized manner with each other and in synchronized manner with the rotating table 16. For example, the first and the second platforms 22, 24 are raised and lowered only when the table 16 is rotating.

During a scanning procedure, the table 16 rotates the cargo container 100 about the axis 20 of rotation, while the first and the second platforms 22, 24 move parallel to the rotation axis 20 of the table 16, and the X-ray source 12 sends an X-ray beam through the cargo container 100 to the X-ray detector 14 (i.e., perpendicular to the rotation axis 20 of the table 16 as shown in the exemplary embodiment of FIGS. 1 and 2). The X-ray beam starts passing through the cargo container 100 at a bottom end of the container 100, and the container 100 is completely scanned when the X-ray beam clears a top end of the container 100, at which time the X-ray source 12 shuts off.

The scanned cargo container 100 is then removed from the table 16, another cargo container 100' is positioned on the table 16 and the table 16 is rotated. The first and the second platforms 22, 24 then move in an opposite direction (i.e., downward in the exemplary embodiment of FIGS. 1 and 2), parallel to the rotation axis 20 of the table 16 and the X-ray source 12 and the X-ray detector 14 are operated to scan the next container 100'. The system 10, therefore, is operated to scan the largest number of cargo containers in the shortest period of time in order to obtain a high throughput of cargo.

The system 10 also includes a conveyor for conveying cargo containers 100 onto and off the table 16. In the exemplary embodiment shown, the conveyer includes a plurality of individual conveyor sections including a motorized entrance conveyor 26, a motorized interim entrance conveyor 28, a motorized interim exit conveyor 30, and a motorized exit conveyor 32. In addition, the table 16 includes a motorized conveyor. The table 16 also includes locks, which are preferably automatically activated and deactivated, for securing the containers 100 thereon during scanning (the following U.S. patents show examples of latches for securing cargo containers in place: U.S. Pat. Nos. 3,810,534; 3,986,460; 4,089,275; 4,349,302; and 5,433,564).

The system 10 further includes a six-sided X-ray containment shield 18 (the top wall is shown removed in FIGS. 1 and 2, while a front wall is shown removed in FIG. 2) for preventing radiation from propagating beyond the shield. The shield 18 includes two sliding doors 34 for allowing passage of a cargo container into and out of the shield. Although not shown, the doors 34 can include motors for automatically opening and closing the doors 34 in synchronization with the first and the second platforms 22, 24, the table 16, the motorized conveyors 26, 28, 30, 32, and the cargo container locks. The X-ray containment shield 18 is configured to occupy as little area and volume as possible in order to reduce the foot print of the X-ray containment space.

Although not shown, the system 10 further includes a data acquisition system for receiving and processing signals generated by the detector array 14, and an X-ray tube control system for supplying power to, and otherwise controlling the operation of, the X-ray source 12. The X-ray tube control system can be, for example, a dual energy X-ray tube control system. The CT scanning system 10 is also preferably provided with a computer for processing the output of the data acquisition system and for generating the necessary signals for operating and controlling the system. The computer can include a CPU and a monitor, and may also include a processing center for respectively processing and displaying information including generated CT images.

In operation, the X-ray source 12 generates from its focal spot a pyramidically shaped beam, often referred to as a "cone" beam X-ray (shown in FIG. 1) that passes through a three dimensional imaging field, through which the cargo container 100 is positioned by the conveyor. After passing through the scanned section of the cargo container 100, the cone beam is received by the detector array 14, which in turn generates signals representative of physical attributes of portions of the cargo container 100 between the focal spot and the respective detector during the measuring interval. By way of example, one physical attribute can be the representative densities of portions of the cargo container 100 as determined as a function of the integral of the attenuation of the radiation beam passing through the container and any object therein. Where a dual energy power supply is utilized, the specific molecular weight of objects such as plastic explosives can be detected. Other physical attributes which may be detected will be evident to those skilled in the art. Thus, the scanning system 10 is not only useful for detecting plastic explosives, but the system can be used to detect other targeted objects, such as firearms and the like.

As the table 16 rotates the cargo container 100 between the X-ray source 12 and the X-ray detector 14, and the first and the second platforms 22, 24 are raised and lowered parallel to the axis 20 of rotation, a plurality of projections are generated at a corresponding plurality of projection angles with each 360° rotation of the table 16. In a well known manner, signals from the detector array 14 can be initially acquired by a data acquisition system, and subsequently processed by a computer.

The central processing unit that controls the X-ray source 12 and the X-ray detector 14 can also be used to control the motor of the table 16, and the motors of the first and the second platforms 22, 24, the motorized conveyors 26, 28, 30, 32, the motors of the doors 34 and the cargo container locks, and synchronize operation of the first and the second platforms 22, 24, the table 16, and the X-ray source 12 and the X-ray detector 14, the motorized conveyors 26, 28, 30, 32, the doors 34 and the cargo container locks.

It should be understood that the embodiments of the present disclosure described herein are merely exemplary and that a person skilled in the art may make variations and modifications to the embodiments described without departing from the spirit and scope of the present disclosures. Because certain changes may be made to the above-described apparatus 10 without departing from the spirit and scope of the present disclosure, all matter contained in the above description or shown in the accompanying drawings shall be interpreted in an illustrative and not a limiting sense. All such equivalent variations and modifications are intended to be included within the scope of this disclosure as defined by the appended claims.

What is claimed is:

1. An X-ray computed tomography scanning system adapted to scan air cargo containers or other larger containers for detection of explosives, drugs, and other contraband, comprising:

a table that rotates about an axis of rotation, wherein the table is sized and adapted to receive and support thereon a cargo container sized and adapted to contain a plurality of pieces of luggage, and wherein the axis of rotation of the table extends in a vertical direction;

an X-ray source linearly movable parallel to the rotation axis of the table on one side of the table;

an X-ray detector linearly movable parallel to the rotation axis of the table on another side of the table, wherein the X-ray source and the X-ray detector are controlled such that they move in a synchronized manner when the table is rotated;

a conveyor for successively conveying cargo containers onto and off of the table;

an X-ray containment shield enclosing the table, the X-ray source, and the X-ray detector, wherein the shield includes doors for allowing passage of a cargo container onto and off of the table via the conveyor; and a data acquisition system including a computer for receiving and processing signals generated by the X-ray detector, wherein the synchronized rotation of the table and linear movement of the X-ray source and the X-ray detector allows the data acquisition system to produce computed tomography images of a cargo container located on the rotating table.

2. A system according to claim 1, wherein the X-ray source is for a dual energy, helical-cone-beam, multi-slice computed tomography X-ray system.

3. A system according to claim 1, wherein the X-ray detector is a two dimensional X-ray detector array.

4. A system according to claim 1, wherein the table is driven about the rotation axis by a drive assembly.

5. A system according to claim 4, wherein the drive assembly comprises a pulley secured to the table, a drive belt connected to the pulley, and a motor connected to the drive belt for causing the drive belt to rotate the pulley and the table.

6. A system according to claim 1, wherein the X-ray source and the X-ray detector are disposed on diametrically opposite sides of the table.

7. A system according to claim 1, wherein a first platform supports the X-ray source and is movable parallel to the rotation axis of the table, and a second platform separate from the first platform supports the X-ray detector and is also movable parallel to the rotation axis of the table.

8. A system according to claim 7, wherein drive mechanisms are used to raise and lower the first and the second platforms.

9. A system according to claim 8, wherein the drive mechanisms comprise rotary motors driving vertically extending screws threaded through bearings secured to the platforms, such that the motors turning the screws cause the platforms to be raised or lowered.

10. A system according to claim 7, wherein the first and the second platforms are raised and lowered only when the table is rotated.

11. A system according to claim 1, wherein the X-ray source and the X-ray detector are controlled such that the X-ray source and the X-ray detector move together in opposite directions parallel to the rotation axis of the table to scan, respectively, successive containers, whereby the system can scan a larger number of containers in a shorter amount of time.

12. A system according to claim 1, wherein the conveyer includes a plurality of individual conveyor sections including an entrance conveyor, an interim entrance conveyor positioned between the table and the entrance conveyor, an exit conveyor, and an interim exit conveyor positioned between the table and the exit conveyor.

13. A system according to claim 12, wherein the conveyors are each motorized.

14. A system according to claim 1, wherein the table includes a motorized conveyor.

15. A system according to claim 1, wherein the table includes locks for securing the containers thereon during scanning.

16. A system according to claim 1, wherein the doors of the shield are adapted to slide open for allowing passage of a container onto and off the table.

17. A system according to claim 1, wherein the containment shield includes four sides and a top panel.

18. A system according to claim 1, wherein the computer controls rotation of the table and movement of the X-ray detector and the X-ray sources and synchronizes the movement of the table, the X-ray detector, and the X-ray source.

19. A system according to claim 1, further comprising motors for causing rotation of the table and movement of the X-ray detector and the X-ray source, motors for opening and closing doors of the X-ray containment shield surrounding the table, the X-ray detector, and the X-ray source to allow a container to be placed on and removed from the table, and motors for driving conveyors for placing and removing containers from the table, wherein the computer controls the motors and synchronizes operation of the table, the X-ray detector, the X-ray source, the doors, and the conveyors.

20. A method of CT scanning cargo containers or other larger containers for detection of explosives, drugs, and other contraband, comprising:
enclosing an X-ray source, an X-ray detector, and a table within an X-ray containment enclosure, wherein the enclosure includes two or more doors adapted to open and close to allow passage of successive cargo containers onto and off of the table;
opening one or more of the doors of the containment enclosure;
conveying one or more cargo containers through doors of the containment enclosure and onto and off of the table, wherein the table is sized and adapted to receive and support thereon a cargo container;
closing one or more of the doors to enclose a container supported on the table within the containment enclosure;
rotating the table and a container to be scanned about an axis of rotation of the table, wherein the axis of rotation of the table extends in a vertical direction;
simultaneously linearly moving the X-ray source and the X-ray detector parallel to the axis of rotation on opposite sides of the container as the container is rotated by the table so as to project
an X-ray beam from the X-ray source, through the container to the X-ray detector as the X-ray source and the X-ray detector move parallel to the axis of rotation; and
receiving and processing signals generated by the X-ray detector, wherein the simultaneous rotation of the table and linear movement of the X-ray source and the X-ray detector allows three dimensional projection and axial computed tomography images of a cargo container located on the rotating table to be produced.

21. A method according to claim 20, wherein the X-ray source is for a dual energy, helical-cone-beam, multi-slice computed tomography X-ray system.

22. A method according to claim 20, wherein the X-ray detector is a two dimensional X-ray detector array.

23. A method according to claim 20, wherein the X-ray source and the X-ray detector are disposed on diametrically opposite sides of the container.

24. A method according to claim 20, wherein the X-ray source and the X-ray detector are moved together in opposite directions parallel to the rotation axis to scan, respectively, successive containers, so that the system can scan a larger number of containers in a shorter amount of time.

25. An X-ray computed tomography scanning system adapted to scan air cargo containers or other larger containers for detection of explosives, drugs, and other contraband, comprising:
an X-ray containment enclosure;
a table, positioned within the X-ray containment enclosure, that rotates about an axis of rotation, wherein the table is sized and adapted to receive and support thereon a cargo container sized and adapted to contain a plurality of pieces of luggage, and wherein the axis of rotation of the table extends in a vertical direction;
an X-ray source linearly movable parallel to the rotation axis of the table on one side of the table within the X-ray containment enclosure, wherein the X-ray source is configured to emit X-rays only when the table is rotating;
an X-ray detector linearly movable parallel to the rotation axis of the table on another side of the table within the containment enclosure, wherein the X-ray source and the X-ray detector are controlled such that they move in a synchronized manner when the table is rotated;
a conveyor for successively conveying cargo containers onto and off of the table, wherein the conveyor includes a plurality of individual conveyor sections, including an entrance conveyor section, an interim entrance conveyor section positioned within the containment enclosure between the table and the entrance conveyor section, an exit conveyor section, and an interim exit conveyor section positioned within the containment enclosure between the table and the exit conveyor section, and wherein the conveyor is configured to move one or more cargo containers while a cargo container is supported on the table within the containment enclosure;
a data acquisition system including a computer for receiving and processing signals generated by the X-ray detector, wherein the synchronized rotation of the table and linear movement of the X-ray source and the X-ray detector allows the data acquisition system to produce computed tomography images of a cargo container located on the rotating table; and wherein the containment enclosure includes two movable doors for allowing passage of one or more cargo containers onto and off of the table via the conveyor.

26. A system according to claim 25, wherein the X-ray source is configured to produce a dual energy, helical-cone-beam.

27. A system according to claim 25, wherein the table is driven about the rotation axis by a drive assembly.

28. A system according to claim 27, wherein the drive assembly comprises a pulley secured to the table, a drive belt connected to the pulley, and a motor connected to the drive belt for causing the drive belt to rotate the pulley and the table.

29. A system according to claim 25, wherein the computer controls rotation of the table and movement of the X-ray detector and the X-ray source and synchronizes the movement of the table, the X-ray detector, and the X-ray source.

* * * * *